(12) United States Patent
Chattopadhyay et al.

(10) Patent No.: US 6,384,246 B1
(45) Date of Patent: May 7, 2002

(54) PROCESS FOR THE PREPARATION OF MALTOL FROM PLANTS BELONGING TO THE GENUS ABIES

(75) Inventors: Sunil Kumar Chattopadhyay; Sachin Srivastava; Koneni Venkata Sashidhara; Vinayah Tripathi; Sushil Kumar, all of Uttar Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/792,030

(22) Filed: Feb. 26, 2001

(51) Int. Cl.$^7$ .................. C07D 309/40; A61K 35/78
(52) U.S. Cl. .................. 549/418; 424/770; 424/774; 424/775; 424/773; 424/778; 424/779; 424/725; 514/460
(58) Field of Search .................. 549/418; 424/770, 424/774, 775, 773, 778, 779, 725; 514/460

(56) References Cited

U.S. PATENT DOCUMENTS 3,501,501 A * 3/1970 Heintz et al. ............... 549/418
5,440,053 A * 8/1995 Fleisher et al. ............. 549/418
5,646,312 A * 7/1997 Arsenault et al. ........... 549/418
5,763,626 A * 6/1998 Guzek et al. ............... 549/418

* cited by examiner

Primary Examiner—Francisco Prats
(74) Attorney, Agent, or Firm—Browdy and Neimark, P.L.L.C.

(57) ABSTRACT

A process has been developed for production of a food flavoring compound maltol which comprises (a) extracting the dried and pulverized leaves of the plants belonging to the genus Abies with an alcohol at 20–40° C. and concentrating the solvent to obtain an alcoholic extract, (b) adsorbing the alcoholic extract with an adsorbent and drying the adsorbed material at a temperature ranging between 20–50° C., (d) partitioning of the adsorbed material between selected solvents consisting of aliphatic hydrocarbon and chlorinated solvent successively, (d) concentrating the chlorinated solvent to a residue and crystallizing it from a suitable organic solvent or mixtures of such solvents to get pure maltol.

13 Claims, No Drawings

PROCESS FOR THE PREPARATION OF MALTOL FROM PLANTS BELONGING TO THE GENUS ABIES

FIELD OF THE INVENTION

The present invention relates to an improved process for the preparation of maltol useful as a food-flavoring compound. Particularly, this invention relates to a processing technology for the isolation of maltol of formula (1) from a readily available plant of the genus Abies. More particularly, the invention relates to a processing technology for the isolation of maltol from the plant *Abies pindrow*.

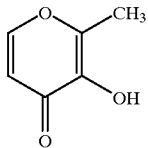

Maltol (1)

BACKGROUND OF THE INVENTION

Maltol (2-methyl-3-hydroxy-4-pyrone) is a heterocyclic aroma chemical of formula (1) used extensively in flavour, fragrance and in some pharmaceutical formulations. It is naturally occurring is many plant species, especially in coniferous trees suck as Larch trees (*Larix decidua* mill), pine trees and pine needles (*Abis alba* mill, pinaceae). Its isolation from the above sources has been reported extensively in the literature (Le Blanc and Akers, "Maltol and ethyl maltol from the Larch trees to successful food additive", Food Technology, pp78–84 (1989); Fleisher and Fleisher, "Water soluble fractions of the essential oils", Perfumer and Flavorist, vol.16, p.37–41 (1991; Heinz et al. U.S. Pat. No. 3,501,501(1970; Brennan et al. U.S. Pat. No. 4,082,717 (1978); Weeks et al. U.S. Pat. No. 4,342,697 (1982); Fleisher et al. U.S. Pat. No. 5,221,756(1993); ibid U.S. Pat. No. 5,440,053 (1995); ibid U.S. Pat. No. 5,441,612 (1995); ibid U.S. Pat. No. 5,641,489 (1997); Arsenault et al. U.S. Pat. No. 5,646,312 (1997); Guzek et al. U.S. Pat. No. 5,763,626 (1998). The presence of maltol in various plant sources has been known for many years and considerable efforts have been made to develop a cost-effective process for its commercial production. The existing techniques are, however, rather complex and the use of the resulting maltol is cost prohibitive.

Heintz et al. (U.S. Pat. No. 3,501,501), described the purification of crude maltol by its co-distillation with ethylene glycol. The drawback of the process includes that the solubility of maltol in ethylene glycol at ambient temperature is about 4%. This prohibits economical maltol recovery from dilute mixtures, effectively eliminating virtually all natural sources. Moreover, the crystallization of maltol from ethylene glycol at ambient temperature is very slow. At very low temperature, the viscosity of ethylene glycol also considerably hampers filtration of maltol from ethylene glycol-maltol mixture. Ethylene glycol derived maltol is also unsuitable for food application, since the removal of toxic ethylene glycol contamination from maltol is rather difficult.

Maltol can be obtained in very small amounts from the destructive distillation products of woods, and by a partially synthetic process from kojic acid which is obtained from fermentation media. However, maltol obtained therefrom is still quite expensive. (Goos and Reiter, "New products from wood carbonization", Industrial and Engineering Chemistry, vol.38, p.132–135 (1946); U.S. Pat. Nos. 3,031,204, 4,082, 717, and 4,343,697 refer to the processes for the synthesis of gammapyrones such as maltol, ethyl maltol and pyromeconic acid).

The recovery of maltol and its purification have also been reported from maltol containing mixture by co-distillation with an aliphatic or cyclo aliphatic hydrocarbon or hydrocarbon mixtures in which maltol is substantially insoluble (Fleicher, A. et al, U.S. Pat. No. 5,221,756).

The disadvantages of the above process include that the process of co-distillation needs a rather sophisticated technological setup, application of vacuum, high pressure steam and necessary handing of flammable liquids. Moreover, during co-distillation, maltol crystallizes directly from the aqueous phase in a micro crystalline form. Thus, maltol obtained from co-distillation process retains substantial quantities (30–40%) of the hydrocarbon which complicates further purification.

Also, process has been reported in which pure maltol is recovered from a mixture containing maltol by extraction into an aqueous solution, optionally in the presence of a substantially water immiscible solvent in which the maltol in the mixture is substantially insoluble. (Guzek, D. et al U.S. Pat. No. 5,763,626).

The drawback of the above process includes that, although maltol is soluble in hot water, it can not be efficiently recovered from plant material by hot water extraction.

Maltol is a known molecule, but it has never been isolated from the plant belonging to the genus Abies which is used in this invention. This plant is available is India in abundance.

OBJECTS OF THE INVENTION

The main object of the present invention is to provide a process for the preparation of maltol useful as food flavoring compound from plants belonging to the genus Abies.

Another object of the present invention is to develop a processing technology for the preparation of maltol from the plant *Abies pindrow*.

Still another object of the present invention is to develop a processing technology for the preparation of maltol which does not use any aqueous extraction of maltol from plant material.

Yet another object of the present invention is to develop a processing technology which does not use any chromatographic separation for its isolation.

SUMMARY OF THE INVENTION

Accordingly, the present invention provides a process for the preparation of maltol from plants belonging to the genus Abies. Particularly, the present invention provides a process for preparation of maltol from the plant *Abies pindrow*.

DESCRIPTION OF THE INVENTION

Accordingly, the present invention provides a process for the preparation of maltol of the formula I shown herebelow from plants belonging to the genus Abies; said process comprising (i) extracting the dried and pulverized parts of the plant with an alcohol at 20–40° C. and concentrating the solvent to obtain an alcoholic extract, (ii) adsorbing the alcoholic extract with an adsorbent and drying the adsorbed material at a temperature ranging from 20–50° C. for 4–12 hours, (iii) extracting the adsorbed material with an aliphatic solvent and then with a chlorinated solvent successively, (iv) concentrating the chlorinated solvent to a residue and crystallizing it from a suitable organic solvent or mixtures of such solvents to get pure maltol.

In an embodiment of the present invention, the plants are selected from the group comprising of *Abies pindrow, Abies spectabilis* and *Abies webbiana*.

More particularly, the present invention provides a process for the preparation of maltol of the formula I shown herebelow from the plant *Abies pindrow*; said process comprising (i) extracting the dried and pulverized parts of the plant with an alcohol at 20–40° C. and concentrating the solvent to obtain an alcoholic extract, (ii) adsorbing the alcoholic extract with an adsorbent and drying the adsorbed material at a temperature ranging from 20–50° C. for 4–12 hours, (iii) extracting the adsorbed material with an aliphatic solvent and then with a chlorinated solvent successively, (iv) concentrating the chlorinated solvent to a residue and crystallizing it from a suitable organic solvent or mixtures of such solvents to get pure maltol.

In an embodiment of the present invention, the plant parts are selected from leaves, stems, roots and flowers.

In another embodiment of the invention, the alcohol used is an alkanol selected from the group comprising of methanol and ethanol.

In still another embodiment of the invention, the adsorbent material is selected from the group comprising of celite, cellulose and/or a mixture thereof.

In still another preferred embodiment of the present invention, the adsorbent material is celite.

In yet another embodiment of the invention, the aliphatic solvent is selected from the group comprising of hexane and petroleum ether.

In yet another preferred embodiment of the present invention, the aliphatic solvent is petroleum ether.

In a further embodiment of the present invention, the chlorinated solvent is selected from the group comprising of chloroform and dichloromethane.

In a preferred embodiment of the present invention, the chlorinated solvent is chloroform.

In one more embodiment of the invention, the solvent for crystallizing maltol is selected from the group comprising of petroleum ether, hexane, acetone, a mixture of toluene-hexane, toluene- petroleum ether, chloroform-hexane, chloroform- petroleum ether, acetone-hexane and cetone-petroleum ether.

In one more preferred embodiment of the present invention, the crystallizing solvent is a mixture of hexane-acetone.

In one another embodiment of the present invention, the yield of maltol obtained by the process of the present invention using the plant *Abies pindrow* is 5% by Wt.

In another embodiment of the present invention, the process of the present invention will produce even more maltol if higher maltol yielding plants are used.

In still another embodiment of the present invention, the process of the present invention can produce better than the best yield so far reported for recovery of maltol from plant sources.

The invention is described in detail in the examples given below which are provided to illustrate the invention and therefore should not be construed to limit the scope of the invention

EXAMPLE 1

Air-dried pulverized leaves of the plant *Abies pindrow* (1 kg) were extracted with MeOH (3 lit×3) at 20–40° C. for three days. MeOH was concentrated under vacuum and the MeOH ext. was adsorbed with celite (600 g.) and the adsorbed material was dried at 20–50° C. for 4–12 hours. The adsorbed material was then extracted with petroleum ether (60–80° C.) (1 lit×3) and chloroform (1 lit×3) successively. Chloroform extract was concentrated under vacuum to a residue and it crystallized out. The crystals were filtered and re-crystallized from petroleum ether-chloroform mixtures to give maltol as needles, yield, 5 grams.

EXAMPLE 2

Air-dried, pulverized leaves of the plant *Abies pindrow* (1 kg) were extracted with EtOH (3 lit×3) at 20–40° C. for three days. EtOH was concentrated under vacuum and the EtOH ext. was adsorbed with cellulose (600 g.) and the adsorbed material was dried at 20–50° C. for 4–12 hours. The adsorbed material was then extracted with hexane (1 lit×3) and dichloromethane (1 lit×3) successively. Dichloromenthane extract was concentrated under vacuum to a residue and it crystallized out. The crystals were filtered and re-crystallized from acetone-petroleum ether to give maltol as needles, yield, 5.1 grams.

EXAMPLE 3

Air-dried, pulverized leaves of the plant *Abies pindrow* (1 kg) were extracted with MeOH (3 lit×3) at room temperature for three days. MeOH was concentrated under vacuum and the MeOH ext. was adsorbed with a mixture of cellulose—celite (600 g.) and the adsorbed material was dried at room temperature. The adsorbed material was then extracted with petroleum ether (60–80° C.) (1 lit×3) and chloroform (1 lit×3) successively. Chloroform extract was concentrated under vacuum to a residue and it crystallized out. The crystals were filtered and re-crystallized from petroleum ether-dichloromethane mixture as to give maltol as needles, yield, 5 grams.

ADVANTAGES

1. The extraction process described in this invention does not use any extreme condition of temperature and pressure, thus it can be adaptable to commercial production of maltol
2. The process described in the invention does not need any chromatographic separation for isolation of maltol, thus the process would be cost effective and adaptable to large-scale production of maltol.
3. The solvents used in extraction process can be recycled and thus the process would again be cost effective.
4. With the availability of high maltol yielding plants which are available globally, the process of the present invention can yield better than the best yield so far reported for maltol from higher plants.

What is claimed is:

1. A process for the preparation of maltol of formula (1) from plants belonging to the genus Abies,

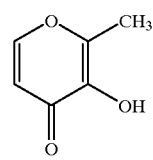

maltol (1)

said process comprising: (a) extracting the dried and pulverized parts of the plant with an alcohol at 20–40° C. and concentrating the solvent to obtain an alcoholic extract, (b) adsorbing the alcoholic extract with an adsorbent and drying the adsorbed material at a temperature ranging from 20–50° C. for 4–12 hours, (c) extracting the adsorbed material with an aliphatic solvent and then with a chlorinated solvent successively, (d) concentrating the chlorinated solvent to a residue and crystallizing it from a suitable organic solvent or mixtures of such solvents to get pure maltol.

2. A process as claimed in claim 1, wherein the plants are selected from the group consisting of *Abies pindrow, Abies webbiana* and *Abies spectabilis.*

3. A process as claimed in claim 1, wherein the plant is *Abies pindrow.*

4. A process as claimed in claim 1, wherein the plant parts are selected from the group consisting of leaves, stems, roots and flowers.

5. A process as claimed in claim 1, wherein the alcohol is an alkanol selected from the group consisting of methanol and ethanol.

6. A process as claimed in claim 1, wherein the adsorbent is selected from the group consisting of celite, cellulose and/or a mixture thereof.

7. A process as claimed in claim 1 wherein the adsorbent is celite.

8. A process as claimed in claim 1 wherein the aliphatic solvent is selected from the group consisting of hexane and petroleum ether.

9. A process as claimed in claim 1 wherein the aliphatic solvent is petroleum ether.

10. A process as claimed in claim 1 wherein the chlorinated solvent is selected from the group consisting of chloroform and dischloromethane.

11. A process as claimed in claim 1 wherein the chlorinated solvent is chloroform.

12. A process as claimed in claim 1 wherein the crystallizing solvent is selected from the group comprising of petroleum ether, hexane, acetone, a mixture of toluene-hexane, toluene-petroleum ether, chloroform-hexane, chloroform-petroleum ether, acetone-hexane, acetone-petroleum ether.

13. A process as claimed in claim 1 wherein the crystallizing solvent is a mixture of hexane-acetone.

* * * * *